US010150727B2

(12) United States Patent
Kim et al.

(10) Patent No.: US 10,150,727 B2
(45) Date of Patent: *Dec. 11, 2018

(54) ESTER COMPOUND, PLASTICIZER COMPOSITION INCLUDING THE SAME, PREPARATION METHOD OF THE PLASTICIZER COMPOSITION AND RESIN COMPOSITION INCLUDING THE PLASTICIZER COMPOSITION

(71) Applicant: LG CHEM, LTD., Seoul (KR)

(72) Inventors: Hyun Kyu Kim, Daejeon (KR); Mi Yeon Lee, Daejeon (KR); Seok Ho Jeong, Daejeon (KR); Jeong Ju Moon, Daejeon (KR); Joo Ho Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/039,791

(22) PCT Filed: Feb. 5, 2015

(86) PCT No.: PCT/KR2015/001203
§ 371 (c)(1),
(2) Date: May 26, 2016

(87) PCT Pub. No.: WO2015/119443
PCT Pub. Date: Aug. 13, 2015

(65) Prior Publication Data
US 2016/0376219 A1    Dec. 29, 2016

(30) Foreign Application Priority Data

Feb. 7, 2014 (KR) .................. 10-2014-0014203
Feb. 24, 2014 (KR) .................. 10-2014-0021409
Nov. 7, 2014 (KR) .................. 10-2014-0154390
Feb. 4, 2015 (KR) .................. 10-2015-0017573
Feb. 4, 2015 (KR) .................. 10-2015-0017574
Feb. 4, 2015 (KR) .................. 10-2015-0017581
Feb. 4, 2015 (KR) .................. 10-2015-0017582
Feb. 4, 2015 (KR) .................. 10-2015-0017583
Feb. 4, 2015 (KR) .................. 10-2015-0017584

(51) Int. Cl.
*C07C 69/80* (2006.01)
*C07C 67/03* (2006.01)
*C07C 67/54* (2006.01)
*C08K 5/12* (2006.01)
*C07C 67/08* (2006.01)
*C07C 69/82* (2006.01)
*C08K 5/00* (2006.01)

(52) U.S. Cl.
CPC .............. *C07C 69/80* (2013.01); *C07C 67/03* (2013.01); *C07C 67/08* (2013.01); *C07C 67/54* (2013.01); *C07C 69/82* (2013.01); *C08K 5/0016* (2013.01); *C08K 5/12* (2013.01)

(58) Field of Classification Search
None
See application file for complete search history.

(56) References Cited

U.S. PATENT DOCUMENTS

| 2,936,320 | A | * | 5/1960 | Benoit, Jr. | ............. C07C 69/80 |
| | | | | | 508/480 |
| 2,975,210 | A | | 3/1961 | Raether et al. | |
| 3,324,040 | A | | 6/1967 | Spoor et al. | |
| 3,736,348 | A | | 5/1973 | Gough et al. | |
| 4,216,337 | A | * | 8/1980 | Baba | ...................... C07C 67/08 |
| | | | | | 549/247 |
| 4,620,026 | A | | 10/1986 | Siegel | |
| 4,654,390 | A | | 3/1987 | Siegel | |
| 4,929,749 | A | | 5/1990 | Gupta et al. | |
| 5,686,147 | A | | 11/1997 | Ngoc | |
| 5,739,203 | A | | 4/1998 | Ngoc | |
| 5,840,236 | A | | 11/1998 | Ngoc | |
| 7,361,779 | B1 | | 4/2008 | Holt et al. | |
| 9,714,211 | B2 | * | 7/2017 | Kim | ....................... C07C 67/08 |
| 2007/0027242 | A1 | * | 2/2007 | Storzum | ................. C07C 69/80 |
| | | | | | 524/296 |
| 2011/0308730 | A1 | * | 12/2011 | Walther | .................. C09J 175/04 |
| | | | | | 156/329 |
| 2014/0096703 | A1 | * | 4/2014 | Lee | ........................... C08K 5/12 |
| | | | | | 106/505 |
| 2016/0237244 | A1 | * | 8/2016 | Boeck | ..................... C07C 67/03 |
| 2017/0166724 | A1 | * | 6/2017 | Kim | ......................... C08K 5/12 |
| 2018/0066124 | A1 | * | 3/2018 | Kim | ..................... C08K 5/0016 |

FOREIGN PATENT DOCUMENTS

| CN | 1184136 A | 6/1998 |
| CN | 101668835 A | 3/2010 |

(Continued)

OTHER PUBLICATIONS

National Center for Biotechnology Information. PubChem Compound Database; CID-226527, http://pubchem.ncbi.nlm.nih.gov/compound/226527 (Create Date Mar. 26, 2005, accessed Apr. 29, 2015).

*Primary Examiner* — Joseph D Anthony
(74) *Attorney, Agent, or Firm* — Dentons US LLP

(57) ABSTRACT

The present invention relates to a novel ester-based compound, an ester-based composition including the same, a preparation method of the ester-based composition and a resin composition including the ester-based composition as a plasticizer. The ester-based composition according to an embodiment of the present invention is a composition including a novel isophthalate-based ester compound for a plasticizer prepared by a trans-esterification reaction and a composition including the same. A resin composition using the ester-based composition is eco-friendly and has good physical properties such as tensile strength, elongation rate, migration resistance, volatile resistance, etc.

22 Claims, No Drawings

(56) References Cited

FOREIGN PATENT DOCUMENTS

| | | | |
|---|---|---|---|
| GB | 851753 | A | 10/1960 |
| GB | 1391897 | A | 4/1975 |
| JP | 4981449 | A | 8/1974 |
| JP | 63-150250 | A | 6/1988 |
| JP | 05-295206 | A | 11/1993 |
| JP | 05-295207 | A | 11/1993 |
| JP | 07-157614 | A | 6/1995 |
| JP | 2001-031794 | A | 2/2001 |
| JP | 2012089287 | A | 5/2012 |
| JP | 2012092074 | A | 5/2012 |
| JP | 2012255104 | A | 12/2012 |
| JP | 2013-163676 | A | 8/2013 |
| JP | 2017-506216 | A | 3/2017 |
| KR | 100440738 | B1 | 7/2004 |
| KR | 100868194 | B1 | 11/2008 |
| TW | 375563 | | 12/1999 |
| WO | 2013143881 | A1 | 10/2013 |

\* cited by examiner

ESTER COMPOUND, PLASTICIZER COMPOSITION INCLUDING THE SAME, PREPARATION METHOD OF THE PLASTICIZER COMPOSITION AND RESIN COMPOSITION INCLUDING THE PLASTICIZER COMPOSITION

This application is a National Stage Application of International Application No. PCT/KR2015/001203, filed Feb. 5, 2015, and claims the benefit of Korean Patent Application No. 10-2015-0017581, filed Feb. 4, 2015, and Korean Patent Application No. 10-2015-0017573, filed Feb. 4, 2015, Korean Patent Application No. 10-2015-0017574, filed Feb. 4, 2015, Korean Patent Application No. 10-2015-0017584, filed Feb. 4, 2015, Korean Patent Application No. 10-2015-0017583, filed Feb. 4, 2015, Korean Patent Application No. 10-2015-0017582, filed Feb. 4, 2015, Korean Patent Application No. 10-2014-0154390, filed Nov. 7, 2014, Korean Patent Application No. 10-2014-0021409, filed Feb. 24, 2014, and Korean Patent Application No. 10-2014-0014203, filed Feb. 7, 2014, the contents of which are incorporated herein by reference in their entirety for all purposes as if fully set forth below.

TECHNICAL FIELD

The present invention relates to a novel ester compound, an ester composition including the same, a preparation method of the plasticizer composition and a resin composition including the plasticizer composition as a plasticizer, and more particularly, to an ester composition including three kinds of isophthalate-based compounds, a preparation method of the plasticizer composition and a resin composition including the plasticizer composition as a plasticizer.

BACKGROUND ART

Generally, a plasticizer is a corresponding ester obtained by the reaction of an alcohol with a polycarboxylic acid such as phthalic acid and adipic acid. Commercially significant examples include an adipate of C8, C9 and C10 alcohol such as di(2-ethylhexyl)adipate, diisononyl adipate and diisodecyl adipate; and a phthalate of C8, C9 and C10 alcohol such as di(2-ethylhexyl)phthalate, diisononyl phthalate and diisodecyl phthalate.

Particularly, the di(2-ethylhexyl)phthalate is used for manufacturing plastisol and a toy, a film, shoes, a paint, a flooring material, gloves, a wall paper, a synthetic leather, a sealant, tarpaulin, a coating agent of the bottom of a vehicle, a furniture, a foamed mat and a soundproof panel via a dry mixing, and may be used for manufacturing an outer packing and insulation of a PVC cable, and for producing other calendered PVC products with plasticity.

Now, di-(2-ethylhexyl)phthalate, etc. are widely used as an ester-based plasticizer, however these compounds are environmental hormones disturbing endocrine system and are harmful to a human body, and have a limit in improving the processability of a resin, absorption rate with a resin, the degree of migration loss and heat stability.

Thus, the development on an ester compound which is eco-friendly, sufficiently improves all physical properties including the processability of a resin, the absorption rate with a resin, the degree of migration loss, heat stability, etc., and a method of preparing the same is required.

DISCLOSURE OF THE INVENTION

Technical Problem

A technical task intend to solve in the present invention is to provide a novel ester-based compound.

Another technical task to solve in the present invention is to provide an ester-based composition having good plasticizing efficiency and improved processability of a resin and providing good physical properties when prescribing a sheet and a compound such as a cable, an interior material of a vehicle, a film, a sheet, a tube, a wall paper, a toy, a flooring material, etc.

Another technical task to solve in the present invention is to provide a preparation method of the ester-based composition.

Final technical task to solve in the present invention is to provide a resin composition including the ester-based composition as a plasticizer.

Technical Solution

To solve the aspect of the present invention, there is provided an ester composition including the compounds of the following Formula 1, Formula 2 and Formula 3.

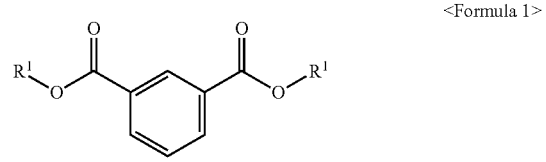

<Formula 1>

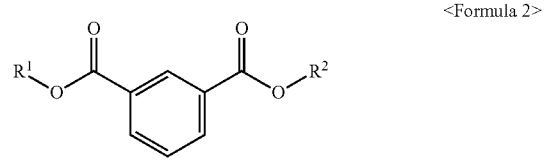

<Formula 2>

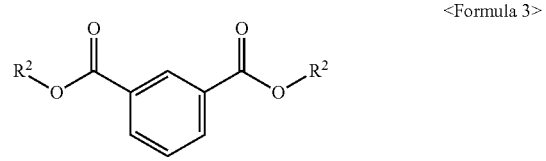

<Formula 3>

In the above Formulae 1 to 3, $R^1$ and $R^2$ are independently $C_1$-$C_{20}$ alkyl, and $R^1$ and $R^2$ are not the same.

In addition, there is provided in the present invention a preparation method of the ester composition including conducting a trans-esterification reaction of a compound of the following Formula 3 with a first alcohol of the following Formula 4.

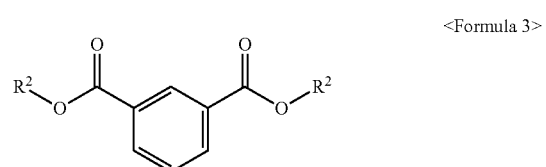

<Formula 3>

-continued

  <Formula 4>

In the above formulae, $R^1$ and $R^2$ are independently $C_1$-$C_{20}$ alkyl, and $R^1$ and $R^2$ are not the same.

Further, there is provided in the present invention at least one ester-based compound selected from the group consisting of compounds of the following formulae.

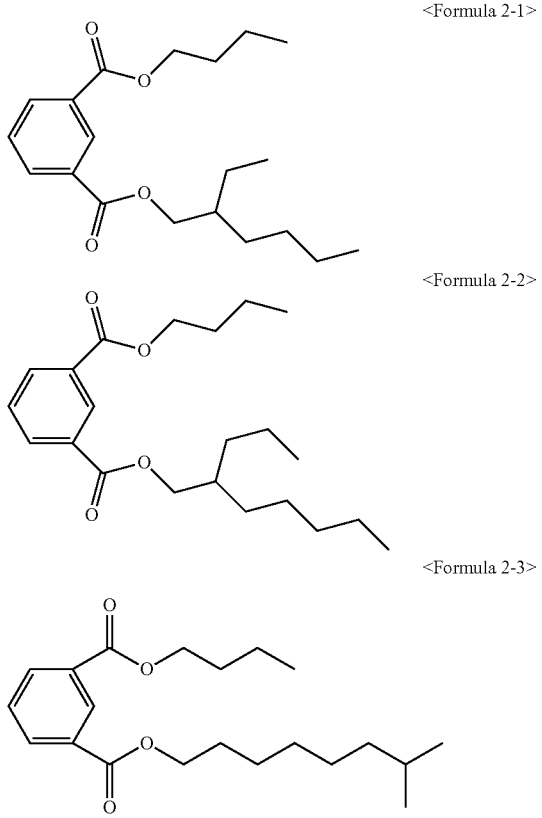

<Formula 2-1>

<Formula 2-2>

<Formula 2-3>

Further, there is provided in the present invention a resin composition including the ester-based composition as a plasticizer and a resin.

Advantageous Effects

The ester compound according to an embodiment of the present invention improves plasticization efficiency and the processability of a resin when used as a plasticizer, and provides good physical properties such as tensile strength, elongation rate, migration resistance, volatile loss, etc.

MODE FOR CARRYING OUT THE INVENTION

Hereinafter, the present invention will be explained in detail to assist the understanding of the present invention.

It will be understood that terms or words used in the present disclosure and claims should not be interpreted as having a meaning that is defined in common or in dictionaries, however should be interpreted in consistent with the technical scope of the present invention based on the principle that inventors may appropriately define the concept of the terms to explain the invention at his best method.

According to an embodiment of the present invention, an ester-based composition including the following Formula 1, Formula 2 and Formula 3 is provided.

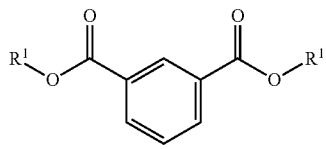

<Formula 1>

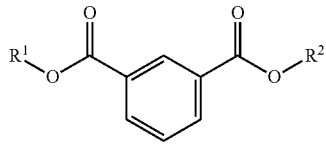

<Formula 2>

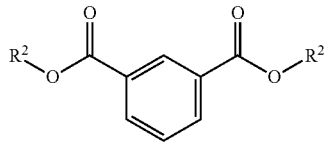

<Formula 3>

In the above Formulae 1 to 3, $R^1$ and $R^2$ are independently $C_1$-$C_{20}$ alkyl, and $R^1$ and $R^2$ are not the same.

The ester-based composition according to an embodiment of the present invention is characterized in including the isophthalate-based compounds of the above Formulae 1 to 3. That is, the ester composition includes an isophthalate-based ester compound in which ester groups (—COO—) are present at positions 1 and 3 in a benzene ring, that is, at a meta position, is more eco-friendly, has better physical properties including tensile strength, elongation rate, migration loss, volatile loss, etc., and has good processability and workability of a product when compared to a phthalate-based ester compound having ester groups (—COO—) at other positions, for example, an ortho position (positions 1 and 2 in a benzene ring) or a para position (positions 1 and 4 in a benzene ring).

In contrast, a phthalate-based compound in which ester groups are present at an ortho position (positions 1 and 2 in a benzene ring) is an environmental hormone disturbing endocrine system and harmful to a human body, and have a limit in improving the processability of a resin, absorption rate with a resin, the degree of migration loss, and heat stability.

In addition, terephthalate-based ester compound having ester groups at para position has relatively deteriorated compatibility and combination stability with the resin due to the linear structure thereof, and these defects may be adversely affecting factors to the processability and workability of a product.

In the case of using the ester-based compound according to an embodiment of the present invention as the plasticizer of the resin composition, equivalent tensile strength and elongation rate may be secured when compared to a common phthalate-based compound widely used as a plasticizer. In addition, volatile loss may be decreased, and migration resistance may be markedly excellent.

According to an embodiment of the present invention, in the above Formulae 1 to 3, $R^2$ may be an alkyl having a more carbon atoms than $R^1$.

According to another embodiment of the present invention, in the above Formulae 1 to 3, $R^1$ is a non-branch type alkyl, and $R^2$ may be a branch type alkyl.

The compound of Formula 1 is an alkyl substituted isophthalate-based compound of a non-hybrid and non-branch type, the compound of Formula 2 is an alkyl substituted isophthalate-based compound of a hybrid and branch type, and the compound of Formula 3 is an alkyl substituted isophthalate-based compound of a non-hybrid and branch type.

According to an embodiment of the present invention, a compound in which $R^1$ is a non-branch type, and $R^2$ is a branch type may have improved hardness, tensile strength and elongation rate when compared to a compound in which both $R^1$ and $R^2$ have a branch type or a non-branch type. In addition, the productivity and processability of a final product may be improved due to the improved tensile strength and elongation rate.

The term "non-hybrid and non-branch type" used in the present invention refers to a structure in which $R^1$ and $R^2$ alkyl groups substituted in ester groups (—COO—) present at positions 1 and 3, that is, a meta position of a benzene ring are the same and two linear hydrocarbons without branched chains are included, if not specifically defined.

In addition, the term "hybrid and branch type" used in the present invention refers to a structure in which $R^1$ and $R^2$ alkyl groups substituted in ester groups (—COO—) present at positions 1 and 3, that is, a meta position of a benzene ring are different from each other and one kind of a branched chain is included. For example, one alkyl group of the $R^1$ and $R^2$ alkyl groups is a branch type alkyl group, other alkyl group is a non-branch type alkyl group, if not specifically defined.

In addition, in an isophthalate-based compound substituted with hybrid and branch type alkyl groups, the branch type alkyl group may be the same as the branch type alkyl group of the isophthalate-based compound substituted with the non-hybrid and branch type alkyl group, and the non-branch type alkyl group may be the same as the non-branch type alkyl group of the isophthalate-based compound substituted with the non-hybrid and non-branch type alkyl group.

Further, the term "non-hybrid and branch type" used in the present invention refers to a structure in which $R^1$ and $R^2$ alkyl groups substituted in ester groups (—COO—) present at positions 1 and 3, that is, a meta position of a benzene ring are the same and at least two branched chains are included, if not specifically defined.

The substituted alkyl may be, for example, a hydrocarbon having 1 to 20 carbon atoms and particularly, $R^1$ may be $C_3$-$C_{10}$ alkyl, and $R^2$ may be at least one independently selected from $C_6$-$C_{12}$ hydrocarbon, and $R^1$ and $R^2$ may be different from each other in consideration of the processability according to fast absorption rate with a resin (plasticizing efficiency) and the degree of migration loss.

According to another embodiment of the present invention, in the above Formulae 1 to 3, $R^1$ may be $C_3$-$C_5$ alkyl, and $R^2$ may be $C_6$-$C_{12}$ alkyl, and more particularly, $R^2$ may be selected from ethylhexyl, isononyl, isodecyl and propylheptyl.

Further, the present invention may provide an ester-based compound of the following formulae. The ester compounds of the following formulae may be hybrid type compounds.

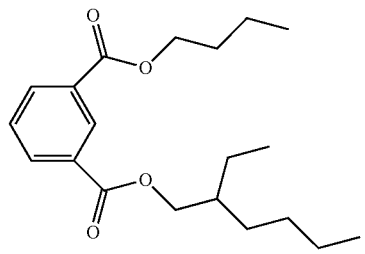

<Formula 2-1>

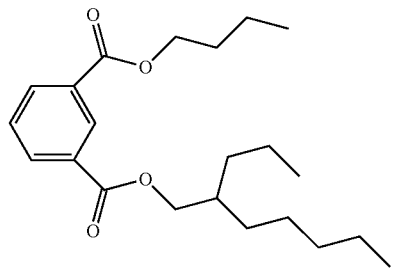

<Formula 2-2>

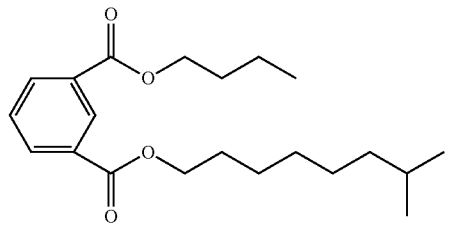

<Formula 2-3>

According to an embodiment of the present invention, the ester-based composition may include the compounds of the following Formulae 1-1, 2-1 and 3-1.

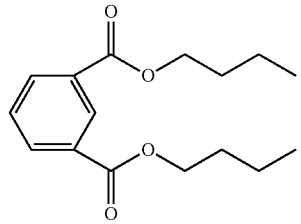

<Formula 1-1>

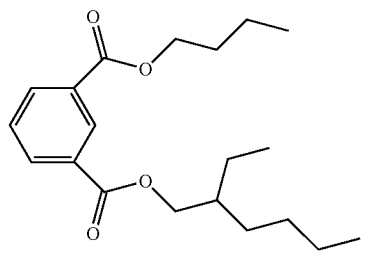

<Formula 2-1>

<Formula 3-1>

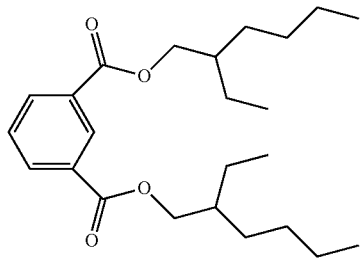

According to an embodiment of the present invention, the ester-based composition may include the compounds of the following Formulae 1-1, 2-2 and 3-2.

<Formula 1-1>

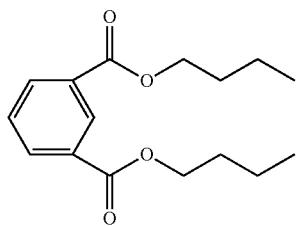

<Formula 2-2>

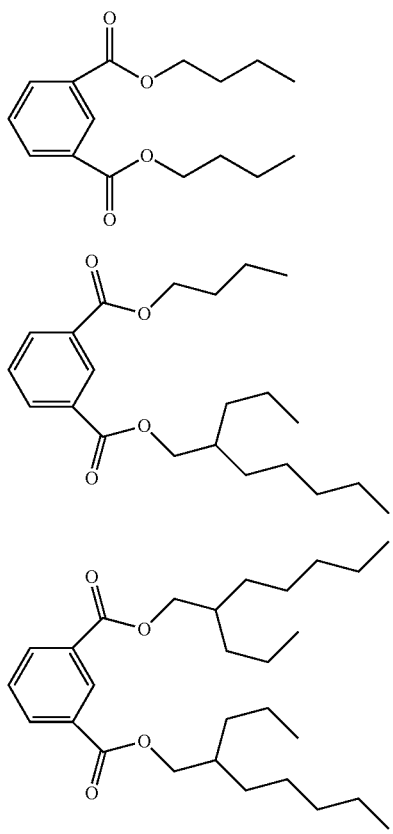

<Formula 3-2>

According to an embodiment of the present invention, the ester-based composition may include the compounds of the following Formulae 1-1, 2-3 and 3-3.

<Formula 1-1>

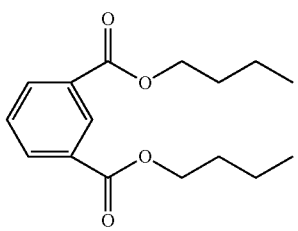

<Formula 2-3>

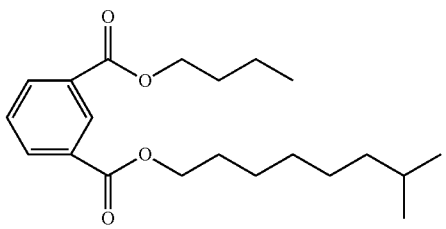

<Formula 3-3>

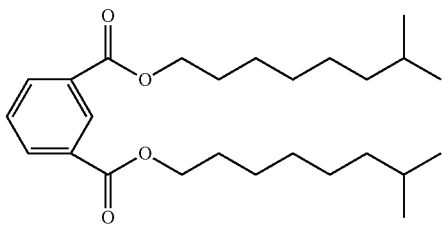

According to an embodiment of the present invention, the ester-based composition may include the compounds of the following Formulae 1-1, 2-4 and 3-4.

<Formula 1-1>

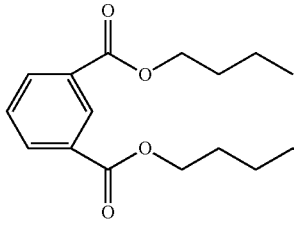

<Formula 2-4>

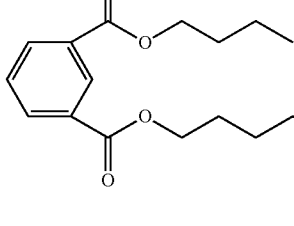

<Formula 3-4>

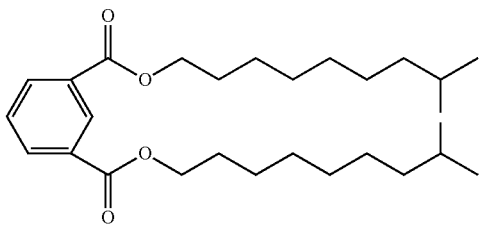

According to an embodiment of the present invention, the compounds of Formula 1, Formula 2 and Formula 3 may be included in an amount ratio of 0.5 to 50 wt %, 0.5 to 70 wt % and 0.5 to 85 wt % with respect to the total amount of the ester composition, respectively, and particularly, in an amount ratio of 0.5 to 50 wt %, 10 to 50 wt % and 35 to 80 wt %.

According to an embodiment of the present invention, the mixing ratio of the total amount of the non-hybrid type compounds of Formulae 1 and 3 and the hybrid type compound of Formula 2 may be 95:5 to 30:70, and preferably, 90:10 to 60:40 by weight.

According to an embodiment of the present invention, the ester-based composition includes the isophthalate-based compounds of Formulae 1 to 3 in the above-described specific amount range and so, is eco-friendly and has short absorption rate and short melting time with respect to a resin to improve the processability of the resin. In addition, physical properties such as hardness, tensile strength, elongation rate, migration loss, sheet volatile loss, heat stability, QUV, etc. may be further improved.

The ester-based composition according to an embodiment of the present invention may be an ether-free plasticizer, and in this case, plasticizing efficiency is good, and workability is good.

Ether-free composition means an ester-based composition in which an ether component included in the composition is 1,000 ppm and less, 100 ppm and less, or 10 ppm and less.

According to an embodiment of the present invention, there is provided a preparation method of the ester-based composition including conducting a trans-esterification reaction of a compound of the following Formula 3 with a first alcohol of the following Formula 4.

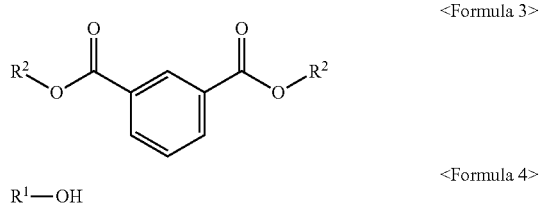

<Formula 3>

<Formula 4>

R¹—OH

In the above formulae, $R^1$ and $R^2$ are independently $C_1$-$C_{20}$ alkyl, and $R^1$ and $R^2$ are not the same.

The term "trans-esterification reaction" used in the present invention means a reaction is conducted between an alcohol and an ester as in the following Reaction 1, and R''' of the ester and R' of the alcohol are interchanged.

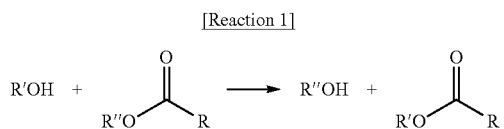

[Reaction 1]

According to an embodiment of the present invention, by conducting the trans-esterification reaction, the compound of Formula 1 may be produced when the alkoxide of the first alcohol of Formula 4 attacks two carbon atoms of the ester group (RCOOR") of the compound of Formula 3, the compound of Formula 2 may be produced when the alkoxide attacks one carbon atom of the ester group (RCOOR") of the compound of Formula 3, and the compound of Formula 3 may remain as an unreacted part.

In addition, the trans-esterification reaction may not induce defects concerning waste water when compared to an esterification reaction between acid-alcohol, and may not induce defects generated when using an acid catalyst because the trans-esterification reaction may be conducted without a catalyst.

According to an embodiment of the present invention, through the trans-esterification reaction, the compound of Formula 1, the compound of Formula 2 and the compound of Formula 3 may be produced in an amount of 0.5 to 50 wt %, 0.5 to 70 wt % and 0.5 to 85 wt %, respectively, with respect to the total amount of the ester-based composition, and particularly in an amount of 0.5 to 50 wt %, 10 to 50 wt % and 35 to 80 wt %.

In the above-described range, an ester-based composition having high process efficiency as a plasticizer and having good processability and absorption rate may be obtained.

According to an embodiment of the present invention, the ester-based composition prepared by the trans-esterification reaction may include all of the compound of Formula 1, the compound of Formula 2 and the compound of Formula 3, and the composition of the ester-based composition may be controlled according to the amount added of the first alcohol of Formula 4.

According to an embodiment of the present invention, the amount added of the first alcohol of Formula 4 may be 0.1 to 89.9 parts by weight, particularly, 3 to 50 parts by weight, and more particularly, 5 to 40 parts by weight with respect to 100 parts by weight of the compound of Formula 3.

According to an embodiment of the present invention, as the amount added of the first alcohol of Formula 4 increases, the mole fraction of the compound of Formula 3 participating in the trans-esterification reaction may be increased, and the amount of the compound of Formula 1 and the compound of Formula 2 may be increased in the ester-based composition.

In addition, the amount of the unreacted compound of Formula 3 may be decreased correspondingly.

According to an embodiment of the present invention, the molar ratio of the compound of Formula 3 and the first alcohol of Formula 4 may be, for example, 1:0.005 to 5.0, 1:0.05 to 2.5, or 1:0.1 to 1.0, and in this range, an ester-based composition having high process efficiency and processability improving effects may be obtained.

According to an embodiment of the present invention, the trans-esterification reaction may preferably be conducted under the reaction temperature of 120° C. to 190° C., preferably 135° C. to 180° C., and more preferably, 141° C. to 179° C., for from 10 minutes to 10 hours, preferably from 30 minutes to 8 hours, and more preferably from 1 to 6 hours. Within the temperature range and the time period range, an ester-based composition having a desired composition may be effectively obtained. In this case, the reaction time may be calculated after elevating the temperature from the time of attainment of the reaction temperature.

According to an embodiment of the present invention, the trans-esterification reaction may be conducted in the presence of an acid catalyst or a metal catalyst, and in this case, the reaction time may be decreased.

The acid catalyst may be sulfuric acid, methanesulfonic acid, p-toluenesulfonic acid, etc., and the metal catalyst may be an organometallic catalyst, a metal oxide catalyst, a metal salt catalyst, a metal itself, etc.

The metal component may be at least one selected from the group consisting of tin, titanium and zirconium, or a mixture of at least two thereof.

In addition, according to an embodiment of the present invention, a removing process for removing the unreacted alcohol and reaction by-products, for example, the compound of Formula 3 by distillation may be further included after conducting the trans-esterification reaction.

The distillation may be, for example, two-step distillation for separating the first alcohol of Formula 4 from the by-products using the difference between boiling points thereof.

In another embodiment, the distillation may be mixed distillation. In this case, the ester-based composition may be relatively stably secured with desired composition. The mixed distillation means the distillation of butanol and the by-products at the same time.

Meanwhile, the compound of Formula 3 used in the trans-esterification reaction of the present invention may be obtained by conducting an esterification reaction of the compound of the following Formula 5 with the second alcohol of the following Formula 6 or a mixture of the second alcohol with at least one isomer thereof in the presence of a catalyst.

<Formula 3>

<Formula 5>

<Formula 6>

$R^2$—OH

In the above formulae, $R^2$ is alkyl of $C_1$-$C_{20}$.

The esterification reaction may be conducted under the reaction temperature of 80° C. to 270° C., preferably 150° C. to 250° C., for from 10 minutes to 10 hours, preferably from 30 minutes to 8 hours, and more preferably from 1 to 6 hours. Within the temperature range and the time period range, the compound of Formula 1 may be effectively obtained.

According to an embodiment of the present invention, the catalyst used in the esterification reaction may be an organometallic catalyst including a Sn-based or a Ti-based catalyst, an acid catalyst including a sulfonic acid-based or a sulfuric-based catalyst, or a mixture catalyst thereof, and the kind of the catalyst is not limited.

According to an embodiment of the present invention, the compound of Formula 5 and the second alcohol of Formula 6 (or a mixture of the second alcohol and at least one isomer thereof) may be used in a molar ratio of 1:1 to 7, and preferably, 1:2 to 5.

According to an embodiment of the present invention, the second alcohol of the above Formula 6 may be used by preparing a common method or may be available on the market. When using the commercially available product, the second alcohol of the above Formula 6 may be included as a mixture with at least one isomer thereof, and the amount of the second alcohol of Formula 6:the isomer thereof may be, for example, 50 to 100 parts by weight:0 to 50 parts by weight, and preferably 70 to 100 parts by weight:0 to 30 parts by weight.

For example, when the second alcohol of the above Formula 6 is 2-propylheptane-1-ol, 4-methyl-2-propyl-hexanol of the following Formula 6-1 or 5-methyl-2-propyl-hexanol of the following Formula 6-2 may be included as the isomer thereof.

<Formula 6-1>

<Formula 6-2>

Particularly, the second alcohol of the above Formula 6 or the mixture of the second alcohol and the isomer thereof may be commercially available. For example, in the case of 2-propylheptane-1-ol, CAS No. 10042-59-8, 66256-62-0, 159848-27-8, etc. of BASF Co. including the isomer thereof may be purchased and used, and in the case of isononyl alcohol, CAS No. 68526-84-1 of EXXONMOBILE Co., CAS No. 27458-94-2 (68515-81-1) of KYOWA Co., etc. including the isomer thereof may be purchased and used. However, the present invention is not limited thereto.

According to an embodiment of the present invention, in the case of using the second alcohol of Formula 6 including the isomer, a mixture of the compound of Formula 3 and the isomer thereof may be prepared. Thus, the ester-based composition according to an embodiment of the present invention may further include the compound of the above Formulae 1 to 3, preferably the compound of Formulae 2 and 3 may further include the isomer thereof, respectively.

By the esterification reaction to prepare the compound of the above Formula 3 according to an embodiment of the present invention, the compound of Formula 3 may be prepared with the yield of about 80% and over. Through the trans-esterification reaction of the compound of Formula 3 thus prepared and the first alcohol of the above Formula 4, the ester-based composition having a desired composition may be easily prepared.

Meanwhile, the present invention provides an ester-based composition prepared by the above preparation method.

In addition, the present invention provides a resin composition including the ester-based composition as a plasticizer and a resin.

According to an embodiment of the present invention, the resin may use a known resin in this field. For example, at least one selected from ethylenevinyl acetate, polyethylene, polypropylene, polyvinyl chloride, polystyrene, polyurethane, thermoplastic elastomer and polylactic acid, without limitation.

According to an embodiment of the present invention, the ester-based composition may be included in an amount of 5 to 100 parts by weight on the basis of 100 parts by weight of the resin.

The filler may be 0 to 300 parts by weight, preferably 50 to 200 parts by weight, and more preferably 100 to 200 parts by weight on the basis of 100 parts by weight of the resin.

According to an embodiment of the present invention, the filler may be a known filler in this art, without specific limitation. For example, a mixture of at least one selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate and barium sulfate, may be used.

In addition, according to an embodiment of the present invention, the resin composition may further include other additives such as a stabilizer, as occasion demands.

Each of the other additives such as the stabilizer may be included in an amount of 0 to 20 parts by weight, and preferably 1 to 15 parts by weight on the basis of 100 parts by weight of the resin.

The stabilizer used according to an embodiment of the present invention may be a Ca—Zn-based stabilizer such as a composite stearate of calcium-zinc, without specific limitation.

In addition, according to an embodiment of the present invention, the resin composition may further include at least one plasticizer selected from dioctyl phthalate (DOP), dibutyl phthalate (DBP), dioctyl terephthalate (DOTP), diisononyl phthalate (DINP), diisodecyl phthalate (DIDP) and di-(2-ethylhexyl)terephthalate (DEHTP). The amount of the plasticizer may be 0 to 150 parts by weight and preferably, 5 to 100 parts by weight on the basis of 100 parts by weight of the resin.

According to an embodiment of the present invention, the resin composition has a sol viscosity of 4,000 to 15,000 cp, 5,000 to 11,000 cp, or 6,000 to 9,000 cp, and in this range, stable processability may be secured.

The sol viscosity in this disclosure is measured using a Brookfield (LV type) viscometer, spindle used is #4, and the measurement is conducted at 6 rpm and 12 rpm. A specimen may be a plastisol obtained by mixing 100 phr of PVC (PB900, LG Chem), 75 phr of an ester-based plasticizer, 4 phr of a stabilizer (KSZ111XF), 3 phr of a foaming agent (W1039), 13 phr of $TiO_2$ (TMCA100), 130 phr or $CaCO_3$ (OMYA10), 10 phr of a viscosity lowering agent (Exa-sol) and 1 phr of a dispersing agent (BYK3160), and the specimen is stored at 25° C. for 1 hour and measured.

The resin composition may be a resin composition obtained by decreasing the amount added of the viscosity lowering agent when compared to a common product or a resin composition obtained by excluding the viscosity lowering agent, that is, a viscosity lowering agent free resin composition.

The viscosity lowering agent free composition in this disclosure means a composition not including a viscosity lowering agent for controlling the viscosity of the resin composition at all.

The ester-based composition according to an embodiment of the present invention has short absorption rate and short melting time with respect to the resin, and the processability of the resin may be improved, and good physical properties may be provided when prescribing a sheet and a compound such as a cable, an interior material of a vehicle, a film, a sheet, a tube, a wall paper, a toy, a flooring material, etc.

Particularly, good physical properties may be obtained when prescribing the resin composition including the ester-based composition as a plasticizer as the wall paper sheet.

Hereinafter, embodiments will be explained in detail to particularly explain the present invention. The present invention may, however, be embodied in different forms and should not be construed as limited to the embodiments set forth herein. Rather, these embodiments are provided so that this disclosure will be thorough and complete, and will fully convey the scope of the inventive concept to those skilled in the art.

PREPARATION EXAMPLES, EXPERIMENTAL EXAMPLES, EXAMPLES AND COMPARATIVE EXAMPLES

Preparation Example 1

To a four-necked, 3 liter reactor equipped with a cooler, a water stripper, a condenser, a decanter, a reflux pump, a temperature controller, a stirrer, etc., 498.4 g of purified isophthalic acid (PIA), 1,172.1 g of ethylhexyl alcohol (molar ratio of isophthalic acid:ethylhexyl alcohol was 1:3) and 1.54 g of tetraisopropyl titanate (TIPT) as a titanium-based catalyst (0.3 parts by weight on the basis of 100 parts by weight of isophthalic acid) were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4.5 hours, and the reaction was terminated when an acid value reached 0.01.

After completing the reaction, distillation-extraction under a reduced pressure was conducted for 0.5 to 4 hours to remove unreacted raw materials. To remove the unreacted raw materials to a certain amount degree and less, steam extraction was conducted using steam under a reduced pressure for 0.5 to 3 hours. The temperature of the reactant was lowered to about 90° C., and neutralization treatment was conducted using an alkaline solution. In addition, washing may be conducted, followed by dehydrating the reactant to remove water. A filter medium was inserted to the dehydrated reactant, followed by stirring for a certain time and filtering to finally obtain 1,162 g of di-(2-ethylhexyl) isophthalate (yield 99.0%).

Preparation Example 2

Bis-(2-propylheptyl)isophthalate was obtained by conducting the same procedure described in Preparation Example 1 except for using 2-propylheptyl alcohol (2-propylheptane-1-ol (85-100%), 1-hexanol; 4-methyl-2-propyl (0-15%); 1-hexanol, 5-methyl-2-propyl (0-15%)) (CAS No. 10042-59-8, 66256-62-0 and 159848-27-8 of BASF Co.) instead of ethylhexyl alcohol.

Preparation Example 3

Bis(isononyl)isophthalate was obtained by conducting the same procedure described in Preparation Example 1 except for using isononyl alcohol (CAS No. 68526-84-1 of EXXONMOBILE Co.) instead of ethylhexyl alcohol.

Preparation Example 4

Bis(isodecyl)isophthalate was obtained by conducting the same procedure described in Preparation Example 1 except for using isodecyl alcohol instead of ethylhexyl alcohol.

Example 1

To a reactor equipped with a stirrer, a condenser and a decanter, 1,000 g of di-(2-ethylhexyl)isophthalate (hereinafter, DEHIP) prepared in Preparation Example 1 and 70 g of butanol (7 parts by weight on the basis of 100 parts by weight of DEHIP) were added, and a trans-esterification reaction was conducted under a nitrogen atmosphere at the reaction temperature of 140° C. for 5 hours without a catalyst to produce an ester-based composition including 1.5 wt %, 22.4 wt % and 76.1 wt % of the compounds of the following Formula 1-1, Formula 2-1 and Formula 3-1, respectively.

<Formula 1-1>

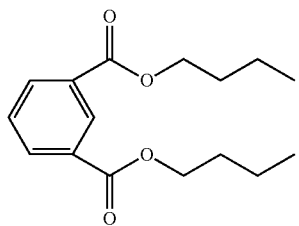

<Formula 2-1>

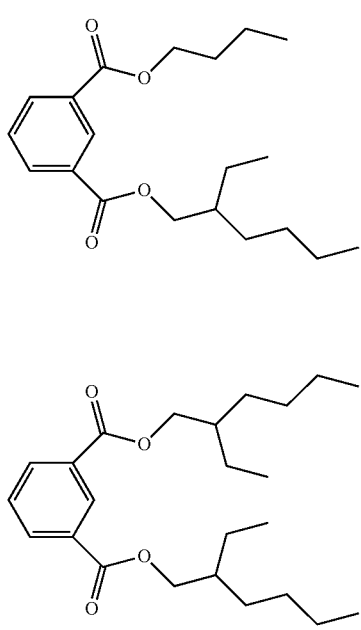

<Formula 3-1>

The reaction product was mixed distilled to remove butanol and 2-ethylhexyl alcohol and to finally prepare an ester-based composition.

Example 2

An ester-based composition including 1.4 wt %, 20.7 wt % and 77.9 wt % of the compounds of the following Formula 1-1, Formula 2-2 and Formula 3-2, respectively, was obtained by conducting the same procedure described in Example 1 except for using bis(2-propylheptyl)isophthalate obtained in Preparation Example 2 instead of di-(2-ethylhexyl)isophthalate (hereinafter, DEHIP) obtained in Preparation Example 1.

<Formula 1-1>

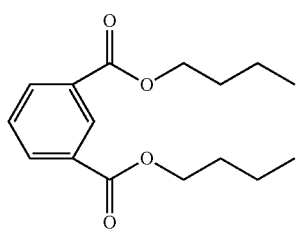

<Formula 2-2>

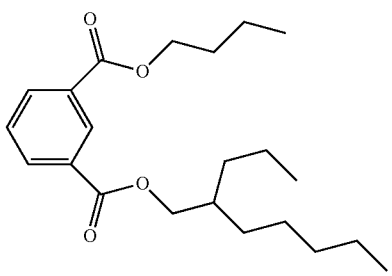

<Formula 3-2>

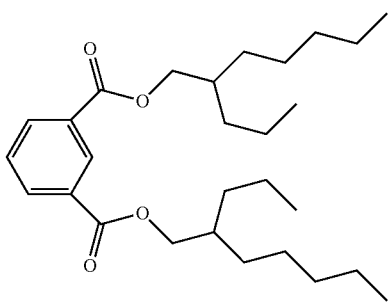

Example 3

An ester-based composition including 1.5 wt %, 21.3 wt % and 77.2 wt % of the compounds of the following Formula 1-1, Formula 2-3 and Formula 3-3, respectively, was obtained by conducting the same procedure described in Example 1 except for using bis(isononyl)isophthalate obtained in Preparation Example 2 instead of di-(2-ethylhexyl)isophthalate (hereinafter, DEHIP) obtained in Preparation Example 1.

<Formula 1-1>

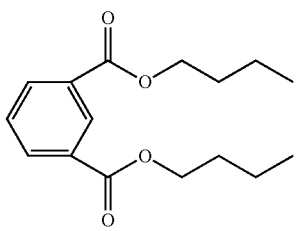

<Formula 2-3>

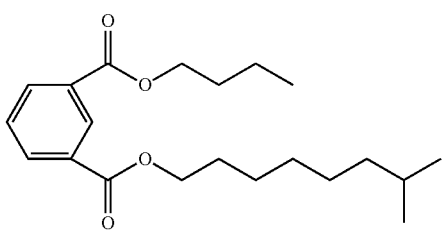

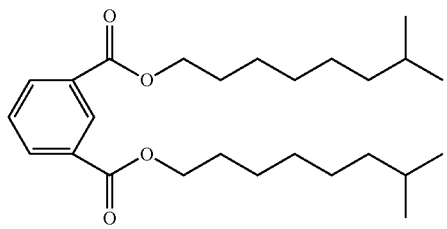

Example 4

An ester-based composition including 1.4 wt %, 20.5 wt % and 78.1 wt % of the compounds of the following Formula 1-1, Formula 2-4 and Formula 3-4, respectively, was obtained by conducting the same procedure described in Example 1 except for using bis(isodecyl)isophthalate obtained in Preparation Example 4 instead of di-(2-ethylhexyl)isophthalate (hereinafter, DEHIP) obtained in Preparation Example 1.

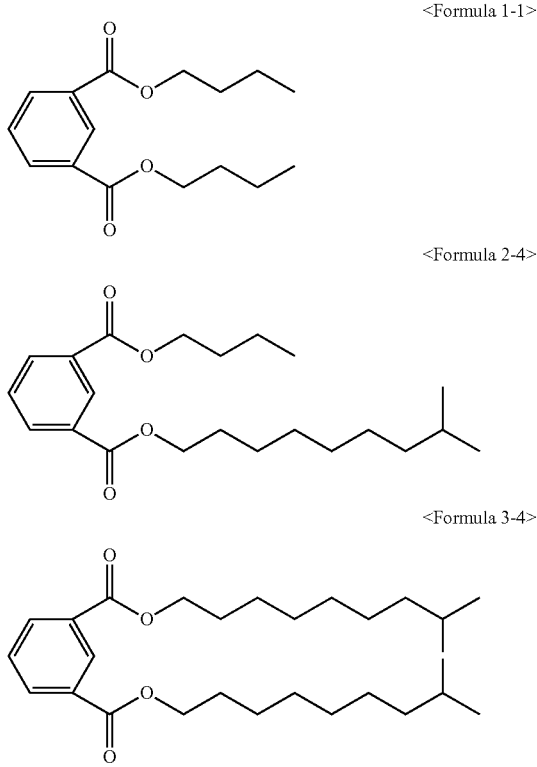

Examples 5 to 13

Ester-based compositions having the composition of the compounds of Formula 1, Formula 2 and Formula 3 were obtained by conducting the same procedure described in Example 1 except for controlling the amount of the butanol as described in the following Table 1.

Comparative Example 1 (Esterification Reaction, Both $R^1$ and $R^2$ have a Branch Type)

To a four-necked, 3 liter reactor equipped with a cooler, a water stripper, a condenser, a decanter, a reflux pump, a temperature controller, a stirrer, etc., 498.4 g of purified isophthalic acid, 1,015.8 g of ethylhexyl alcohol, 1,067 g of 2-propylheptanol and 15 g of methanesulfonic acid (MSA) as a catalyst (3 parts by weight on the basis of 100 parts by weight of PTA) were inserted, followed by slowly elevating the temperature to about 210° C. The generation of water began at about 170° C. An esterification reaction was conducted at the reaction temperature of about 210° C. under an atmospheric pressure while continuously injecting a nitrogen gas for about 4 hours, and the reaction was terminated when an acid value reached 4.

After completing the reaction, distillation-extraction under a reduced pressure was conducted for 0.5 to 4 hours to remove unreacted raw materials. To remove the unreacted raw materials to a certain amount degree and less, steam extraction was conducted using steam under a reduced pressure for 0.5 to 3 hours. The temperature of the reactant was lowered to about 90° C., and neutralization treatment was conducted using an alkaline solution. In addition, washing may be conducted, followed by dehydrating the reactant to remove water. A filter medium was inserted to the dehydrated reactant, followed by stirring for a certain time and filtering to finally obtain 2 wt % of DEHIP, 25 wt % of 2-propylheptyl ethylhexyl isophthalate (PHEHIP) and 73 wt % of bis(2-propylheptyl)isophthalate (DPHIP).

Comparative Example 2 (Terephthalate-based)

A reaction product including 75.5 wt % of di-(2-ethylhexyl)terephthalate (DEHTP), 22.8 wt % of 1-butyl 4-(2-ethylhexyl)terephthalate (hereinafter, BEHTP) and 1.7 wt % of dibutyl terephthalate (hereinafter, DBTP) was obtained by conducting the same procedure described in Preparation Example 1 and Example 1 using terephthalic acid instead of isophthalic acid prepared in Preparation Example 1.

Comparative Example 2 (Phthalate-based)

A reaction product including 75.0 wt % of di-(2-ethylhexyl)terephthalate (DEHP), 22.5 wt % of 1-butyl 4-(2-ethylhexyl)terephthalate (hereinafter, BEHP) and 2.5 wt % of dibutyl phthalate (hereinafter, DBP) was obtained by conducting the same procedure described in Preparation Example 1 and Example 1 using phthalic acid instead of isophthalic acid prepared in Preparation Example 1.

TABLE 1

| | Butanol amount (parts by weight) | Formula 1 (wt %) | Formula 2 (wt %) | Formula 3 (wt %) |
| --- | --- | --- | --- | --- |
| Example 1 (1P) | 7 parts by weight | (Formula 1-1) 1.5 | (Formula 2-1) 22.4 | (Formula 3-1) 76.1 |

TABLE 1-continued

|  | Butanol amount (parts by weight) | Formula 1 (wt %) | Formula 2 (wt %) | Formula 3 (wt %) |
|---|---|---|---|---|
| Example 2 (1P) | 7 parts by weight | (Formula 1-1) 1.4 | (Formula 2-2) 20.7 | (Formula 3-2) 77.9 |
| Example 3 (1P) | 7 parts by weight | (Formula 1-1) 1.5 | (Formula 2-3) 21.3 | (Formula 3-3) 77.2 |
| Example 4 (1P) | 7 parts by weight | (Formula 1-1) 1.4 | (Formula 2-4) 20.5 | (Formula 3-4) 78.1 |
| Example 5 (1P) | 4 parts by weight | (Formula 1-1) 0.6 | (Formula 2-1) 14.4 | (Formula 3-1) 85.0 |
| Example 6 (1P) | 10 parts by weight | (Formula 1-1) 2.8 | (Formula 2-1) 28.4 | (Formula 3-1) 68.8 |
| Example 7 (1P) | 13 parts by weight | (Formula 1-1) 3.1 | (Formula 2-1) 29.8 | (Formula 3-1) 67.1 |
| Example 8 (1P) | 15 parts by weight | (Formula 1-1) 4.8 | (Formula 2-1) 35.1 | (Formula 3-1) 60.1 |
| Example 9 (1P) | 18 parts by weight | (Formula 1-1) 6.9 | (Formula 2-1) 39.4 | (Formula 3-1) 53.7 |
| Example 10 (1P) | 20 parts by weight | (Formula 1-1) 7.9 | (Formula 2-1) 41.1 | (Formula 3-1) 51.0 |
| Example 11 (1P) | 22 parts by weight | (Formula 1-1) 9.0 | (Formula 2-1) 42.7 | (Formula 3-1) 48.3 |
| Example 12 (1P) | 30 parts by weight | (Formula 1-1) 12.5 | (Formula 2-1) 46.3 | (Formula 3-1) 41.2 |
| Example 13 (1P) | 40 parts by weight | (Formula 1-1) 17.9 | (Formula 2-1) 49.4 | (Formula 3-1) 41.7 |
| Comparative Example 1 (1P) | 7 parts by weight | (DEHTP) 2.0 | (PHEHIP) 25.0 | (DPHIP) 73.0 |
| Comparative Example 2 (TP) | 7 parts by weight | (DBTP) 1.7 | (BEHTP) 22.8 | (DEHTP) 75.5 |
| Comparative Example 3 (1P) | 7 parts by weight | (DBP) 2.5 | (BEHP) 22.5 | (DEHP) 75.0 |

Experimental Example 1

Measuring Amount of Ester-based Composition

In the ester-based compositions of Examples 1 to 13 of the present invention and Comparative Examples 1 to 3, the amount (wt %) of each compound was measured using a gas chromatography apparatus of Agilent Co. (Agilent 7890 GC, Column: HP-5, carrier gas: helium).

In the ester-based compositions of Examples 1 to 13, ether was not detected.

Experimental Example 2

Manufacture of Specimen (Sheet) and Evaluation of Performance

For the ester-based compositions prepared in Examples 1 to 13 and Comparative Examples 1 to 3, 55 parts by weight of a plasticizer, 2 parts by weight of a BZ stabilizer (BZ210, Songwon Industries) as an additive and 2 parts by weight of an epoxidized soybean oil (ESO, Songwon Industries) with respect to 100 parts by weight of a polyvinyl chloride resin (PVC, LS 130s) were mixed in a rotational rate of 1,300 rpm at 100° C. A process was conducted using a roll mill at 175 for 4 minutes and using a press at 185° C. for 3 minutes (low pressure) and for 2 minutes and 30 seconds (high pressure) to manufacture a sheet to a thickness of 2 mm.

With respect to the sheet, hardness, tensile strength, elongation rate, migration loss and sheet volatile loss was measured.

The evaluation conditions of each performance were as follows.

Measuring Hardness

Shore hardness (Shore A) at 25° C. was measured using ASTM D2240.

Measuring Tensile Strength

By ASTM D638 method, a specimen was drawn in a cross head speed of 200 mm/min using a test apparatus of U.T.M (manufacturer: Instron, model name: 4466), and a point where the sample was cut was measured. The tensile strength was calculated as follows.

Tensile strength (kgf/cm$^2$)=load value (kgf)/thickness (cm)×width (cm)

Measuring Elongation Rate

By ASTM D638 method, a specimen was drawn in a cross head speed of 200 mm/min using a test apparatus of U.T.M, and a point where the specimen was cut was measured. The elongation rate was calculated as follows.

Elongation rate (%)=length after elongation/initial length×100.

Measuring Migration Loss

According to KSM-3156, a specimen with a thickness of 2 mm and over was obtained, ABS (natural color) was attached onto both sides of the specimen and a load of 1 kgf/cm$^2$ was applied. The specimen was stood in a hot air circulation type oven (80° C.) for 72 hours and then taken out and cooled at room temperature for 4 hours. Then, the ABS attached onto both sides of the specimen was removed, the weights before and after standing in the oven were measured, and the migration loss was calculated by the following equation.

Migration loss (%)={(initial weight of specimen at room temperature−weight of specimen after standing in oven)/initial weight of specimen at room temperature}×100

Measuring Sheet Volatile Loss

The specimen thus manufactured was processed at 70° C. for 72 hours, and the weight of the specimen was measured. Volatile loss (wt %)=initial weight of specimen−(weight of specimen after processing at 100° C. for 168 hours)/initial weight of specimen×100

TABLE 2

| | | Example/Comparative Example | | | | |
|---|---|---|---|---|---|---|
| | | Example 1 | Example 2 | Example 3 | Example 4 | Comparative Example 1 |
| $R^1$ and $R^2$ | | $R^1$: butyl $R^2$: ethylhexyl | $R^1$: butyl $R^2$: propylheptyl | $R^1$: butyl $R^2$: isononyl | $R^1$: butyl $R^2$: isodecyl | $R^1$: ethylhexyl $R^2$: propylheptyl |
| Reaction | | Trans-esterification | Trans-esterification | Trans-esterification | Trans-esterification | Esterification reaction |
| Physical properties | Hardness (Shore A) | 87.0 | 90.5 | 88.5 | 90.8 | 91.8 |
| | Tensile strength (kg/cm$^2$) | 223.2 | 231.2 | 225.7 | 230.1 | 232.9 |
| | Elongation rate (%) | 306.5 | 287.3 | 290.6 | 288.5 | 278.0 |

The results of the above Table 2 are obtained by measuring the physical properties using the ester-based compositions of Examples 1 to 4 and Comparative Example 1 according to the trans-esterification reaction or esterification reaction, and branch/non-branch type of $R^1$ and $R^2$.

As shown in the above Table 2, the ester-based compositions of Examples 1 to 4 of the present invention prepared by the trans-esterification reaction have markedly improved hardness, tensile strength and elongation rate when compared to those of the ester-based composition of Comparative Example 1.

When particularly examining, the ester-based compositions of Examples 1 to 4 of the present invention, particularly, the ester-based compositions of Examples 1 to 4 in which $R^1$ is a non-branch type, and $R^2$ is a branch type by the trans-esterification reaction have better hardness, tensile strength and elongation rate when compared to the ester-based composition of Comparative Example 1 in which both $R^1$ and $R^2$ have a branch type.

For example, the hardness of the ester-based compositions of Examples 1 to 4 is decreased by 5% and over when compared to the ester-based composition of Comparative Example 1. Since the hardness is decreased as in the examples of the present invention, good processability and the stabilization of workability may be provided when applied in a practical product.

In addition, it would be known that the elongation rate is increased by about 4% and over for the ester-based compositions of Examples 1 to 4 when compared to that of the ester-based composition of Comparative Example 1.

TABLE 3

| | Butanol amount | Hardness (Shore A) | Tensile strength (kg/cm$^2$) | Elongation rate (%) | Migration loss (%) |
|---|---|---|---|---|---|
| Example 5 | 4 parts by weight | 87.5 | 230.5 | 309.5 | 0.08 |
| Example 6 | 10 parts by weight | 87.0 | 220.3 | 305.6 | 0.11 |
| Example 7 | 13 parts by weight | 86.7 | 220.1 | 306.7 | 0.13 |

TABLE 3-continued

| | Butanol amount | Hardness (Shore A) | Tensile strength (kg/cm$^2$) | Elongation rate (%) | Migration loss (%) |
|---|---|---|---|---|---|
| Example 8 | 15 parts by weight | 86.5 | 219.5 | 304.5 | 0.13 |
| Example 9 | 18 parts by weight | 86.4 | 219.1 | 307.5 | 0.14 |
| Example 10 | 20 parts by weight | 86.2 | 219.2 | 305.3 | 0.16 |
| Example 11 | 22 parts by weight | 85.8 | 219.0 | 296.5 | 0.30 |
| Example 12 | 30 parts by weight | 83.5 | 205.3 | 285.1 | 0.60 |
| Example 13 | 40 parts by weight | 83.5 | 197.6 | 272.3 | 1.23 |

The above Table 3 shows the hardness, tensile strength, elongation rate and migration resistance of the ester-based compositions of Examples 5 to 13 according to the amount added of butanol.

As shown in the above Table 3, the hardness, tensile strength, elongation rate and migration resistance are markedly changed according to the amount added of butanol.

Particularly, the hardness, tensile strength and elongation rate are relatively improved while the migration resistance is decreased according to the decrease of the amount added of butanol.

Accordingly, the physical properties may be controlled according to use by controlling the amount of butanol, and it would be secured that the ester-based compositions may be usefully applied.

TABLE 4

| | | Example/Comparative example | | |
|---|---|---|---|---|
| | | Example 1 | Comparative Example 2 | Comparative Example 3 |
| | Acid | Isophthalic acid | Terephthalic acid | Phthalic acid |
| | Reaction | Trans-esterification | Trans-esterification | Trans-esterification |
| Physical properties | Hardness (Shore A) | 87.0 | 87.7 | 87.3 |
| | Tensile strength (kg/cm$^2$) | 223.2 | 232.1 | 221.6 |
| | Elongation rate (%) | 306.5 | 278.5 | 304.8 |
| | Migration loss (%) | 0.10 | 0.08 | 1.23 |
| | Volatile loss (%) | 6.20 | 7.52 | 8.96 |

Table 4 shows the results of the hardness, tensile strength, elongation rate and migration resistance of the sheets manufactured using the plasticizers of Example 1 and Comparative Examples 2 and 3 by changing the kinds of an acid.

As shown in the above Table 4, the elongation rate is improved, and the effects of migration resistance and volatile loss are good for the ester-based compositions of the examples of the present invention using an isophthalate-based ester plasticizers when compared to the ester-based compositions of Comparative Examples 2 and 3 using terephthalate-based and phthalate-based ester plasticizers.

Particularly, for the specimen using the isophthalate-based ester plasticizer of the present invention, the elongation rate, migration resistance and volatile loss are improved when compared to the phthalate-based and terephthalate-based ester plasticizer having ester groups at ortho position and para position. Thus, the processability of a resin, absorption rate with the resin, the degree of migration loss and heat stability are improved.

Particularly, the migration resistance of the specimen of Example 1 of the present invention may be decreased 10 times and less when compared to that of Comparative Example 3.

In addition, the volatile loss of the specimen of Example 1 of the present invention may decrease to about 20 to 45% when compared to that of Comparative Examples 2 and 3.

The decrease of the volatile loss as in Comparative Examples 2 and 3 may be a fatal defect in the processability and the stability for a long time of a final product. That is, the increase of the volatile loss means the decrease of the amount of the ester-based composition (plasticizer) present in the specimen and the deterioration of the elongation rate.

Thus, it would be secured that the physical properties of the isophthalate-based ester plasticizer of the present invention are markedly increased when compared to a terephthalate-based and phthalate-based plasticizers.

Preparation Example 5, Examples, Comparative Examples and Experimental Examples

Preparation Example 5

To a four-necked, 3 liter reactor equipped with a cooler, a water stripper, a condenser, a decanter, a reflux pump, a temperature controller, a stirrer, etc., 498.4 g of purified isophthalic acid (PIA), 1,425 g of 2-propylheptanol (2-PH) (BASF Co., including 80-100 wt % of 2-PH, 0-15 wt % of 4-methyl-2-propyl hexanol and 0-15 wt % of 5-methyl-2-propyl-hexanol) (molar ratio of isophthalic acid:2-PH was 1:3) and 1.54 g of tetra isopropyl titanate (TIPT) as a titanium-based catalyst were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4.5 hours, and the reaction was terminated when an acid value reached 0.01.

After completing the reaction, distillation-extraction under a reduced pressure was conducted for 0.5 to 4 hours to remove unreacted raw materials. The reactant was cooled, and neutralization treatment was conducted using an alkaline solution. In addition, the reactant was dehydrated to remove water. A filter medium was inserted to the dehydrated reactant, followed by stirring for a certain time and filtering to finally obtain 1,162 g of di-(2-propylheptyl) isophthalate (yield 99.0%).

Example 14

To a reactor equipped with a stirrer, a condenser and a decanter, 1,000 g of di-(2-propylheptyl)isophthalate (hereinafter, DPHIP) prepared in Preparation Example 5 and 70 g of butanol (7 parts by weight on the basis of 100 parts by weight of DPHIP) were added, and a trans-esterification reaction was conducted under a nitrogen atmosphere at the reaction temperature of 140° C. for 5 hours without a catalyst to produce an ester-based composition including 21.0 wt %, 1.6 wt % and 77.4 wt % of the compounds of the following Formula 2-2, Formula 1-1 and Formula 3-2, respectively.

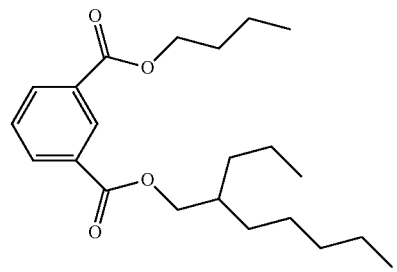

<Formula 2-2>

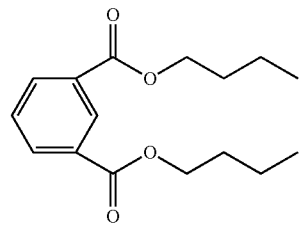

<Formula 1-1>

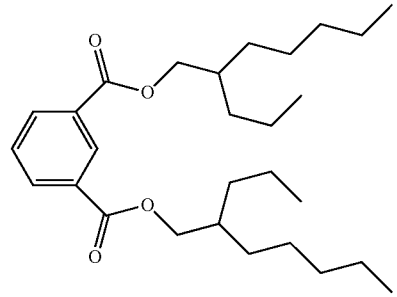

<Formula 3-2>

Examples 15 to 21

Ester-based compositions having the compositions of Formula 2-2, Formula 1-1 and Formula 3-2 in the following Table 5 were obtained by conducting the same procedure described in Example 14 except for controlling the amount of butanol as described in the following Table 5.

Comparative Example 4 (Terephthalate-based)

A reaction product including 75.4 wt % of di-(2-propylheptyl)terephthalate (DPHTP), 23.2 wt % of 1-butyl 4-(2-propylheptyl)terephthalate (hereinafter, BPHTP) and 1.4 wt % of dibutyl terephthalate (hereinafter, DBTP) was obtained by conducting the same procedure described in Preparation Example 2 and Example 14 using terephthalic acid instead of isophthalic acid prepared in Preparation Example 2.

Comparative Example 5 (Phthalate-based)

A reaction product including 74.5 wt % of di-(2-propylheptyl)phthalate (DPHP), 22.1 wt % of 1-butyl 4-(2-propylheptyl)phthalate (hereinafter, BPHP) and 3.4 wt % of dibutyl phthalate (hereinafter, DBP) was obtained by conducting the same procedure described in Preparation Example 2 and an example using phthalic acid instead of isophthalic acid prepared in Preparation Example 2.

TABLE 5

|  | Butanol amount (parts by weight) | Formula 1-1 (wt %) | Formula 2-2 (wt %) | Formula 3-2 (wt %) |
|---|---|---|---|---|
| Example 14 (1P) | 7 parts by weight | Formula 1-1 1.6 | Formula 2-2 21.0 | Formula 3-2 77.4 |
| Example 15 (1P) | 4 parts by weight | Formula 1-1 0.6 | Formula 2-2 14.7 | Formula 3-2 84.7 |
| Example 16 (1P) | 10 parts by weight | Formula 1-1 2.6 | Formula 2-2 28.5 | Formula 3-2 68.9 |
| Example 17 (1P) | 15 parts by weight | Formula 1-1 5.2 | Formula 2-2 36.1 | Formula 3-2 58.7 |
| Example 18 (1P) | 20 parts by weight | Formula 1-1 8.0 | Formula 2-2 41.3 | Formula 3-2 50.7 |
| Example 19 (1P) | 22 parts by weight | Formula 1-1 9.2 | Formula 2-2 43.0 | Formula 3-2 47.8 |
| Example 20 (1P) | 30 parts by weight | Formula 1-1 12.8 | Formula 2-2 46.5 | Formula 3-2 40.7 |
| Example 21 (1P) | 40 parts by weight | Formula 1-1 18.5 | Formula 2-2 49.8 | Formula 3-2 31.7 |
| Comparative Example 4 (TP) | 7 parts by weight | (DBTP) 1.4 | (BPHTP) 23.2 | (BPHTP) 75.4 |
| Comparative Example 5 (P) | 7 parts by weight | (DBP) 3.4 | (BPHP) 22.1 | (DPHP) 74.5 |

Experimental Example 3

Measuring Amount of Ester-based Composition

In the ester-based compositions of Examples 14 to 21 of the present invention and Comparative Examples 4 to 5, the amount (wt %) of each compound was measured using a gas chromatography apparatus of Agilent Co. (Agilent 7890 GC, column: HP-5, carrier gas: helium).

In the ester-based compositions of Examples 14 to 21, ether was not detected.

Experimental Example 4

Manufacture of Specimen (Sheet) and Evaluation of Performance

For the ester-based composition prepared in Examples 14 to 21 and Comparative Examples 3 to 5, 55 parts by weight of a plasticizer, 2 parts by weight of a BZ stabilizer (BZ210, Songwon Industries) as an additive and 2 parts by weight of an epoxidized soybean oil (ESO, Songwon Industries) with respect to 100 parts by weight of a polyvinyl chloride resin (PVC, LS 130s) were mixed in a rotational rate of 1,300 rpm at 100° C. A process was conducted using a roll mill at 175° C. for 4 minutes and using a press at 185° C. for 3 minutes (low pressure) and for 2 minutes and 30 seconds (high pressure) to manufacture a sheet with a thickness of 2 mm.

With respect to the sheet, hardness, tensile strength, elongation rate, migration loss and sheet volatile loss were measured. The results are illustrated in Tables 6 and 7.

TABLE 6

|  | Butanol amount | Hardness (Shore A) | Tensile strength (kg/cm$^2$) | Elongation rate (%) | Migration loss (%) |
|---|---|---|---|---|---|
| Example 15 | 4 parts by weight | 92.6 | 268.7 | 256.3 | 0.02 |
| Example 16 | 10 parts by weight | 91.2 | 249.5 | 267.5 | 0.03 |
| Example 17 | 15 parts by weight | 90.3 | 235.1 | 280.5 | 0.03 |
| Example 18 | 20 parts by weight | 88.7 | 218.6 | 296.8 | 0.05 |
| Example 19 | 25 parts by weight | 86.9 | 213.2 | 316.4 | 0.07 |
| Example 20 | 30 parts by weight | 85.8 | 205.6 | 320.6 | 0.10 |
| Example 21 | 40 parts by weight | 85.0 | 198.3 | 332.3 | 0.18 |

The above Table 6 shows the hardness, tensile strength, elongation rate and migration resistance of the ester-based compositions of Examples 15 to 21 according to the amount added of butanol.

As shown in the above Table 6, the hardness, tensile strength, elongation rate and migration resistance are markedly changed according to the amount added of butanol.

Particularly, the hardness, tensile strength and elongation rate are relatively improved while the migration resistance is decreased according to the decrease of the amount added of butanol.

Accordingly, the physical properties may be controlled according to use by controlling the amount of butanol, and it would be secured that the ester-based compositions may be usefully applied.

TABLE 7

|  |  | Example/Comparative example | | |
|---|---|---|---|---|
|  |  | Example 14 | Comparative Example 4 | Comparative Example 5 |
| Acid |  | Isophthalic acid | Terephthalic acid | Phthalic acid |
| Reaction |  | Trans-esterification | Trans-esterification | Trans-esterification |
| Physical properties | Hardness (Shore A) | 91.8 | 93.5 | 92.0 |
|  | Tensile strength (kg/cm$^2$) | 256.5 | 284.3 | 257.8 |

TABLE 7-continued

| | Example 14 | Comparative Example 4 | Comparative Example 5 |
|---|---|---|---|
| Elongation rate (%) | 260.4 | 235.1 | 255.8 |
| Migration loss (%) | 0.03 | 0.07 | 0.03 |
| Volatile loss (%) | 0.67 | 1.11 | 0.87 |

Table 7 shows the results of the hardness, tensile strength, elongation rate and migration resistance of the sheets manufactured using the plasticizers of Example 14 and Comparative Examples 4 and 5 by changing the kinds of an acid.

As shown in the above Table 7, the elongation rate is improved, and the effects of migration resistance and volatile loss are good for the ester-based compositions of the examples of the present invention using an isophthalate-based ester plasticizers when compared to the ester-based compositions of Comparative Examples 4 and 5 using terephthalate-based and phthalate-based ester plasticizers.

Particularly, for the specimen using the isophthalate-based ester plasticizer of the present invention, the elongation rate, migration resistance and volatile loss are improved when compared to the phthalate-based and terephthalate-based ester plasticizer having ester groups at ortho position and para position. Thus, the processability of a resin, absorption rate with the resin, the degree of migration loss and heat stability are improved.

In addition, the volatile loss of the specimen of Example 14 of the present invention may decrease to about 30 to 65% when compared to that of Comparative Examples 4 and 5.

The increase of the volatile loss as in Comparative Examples 4 and 5 may be a fatal defect in the processability and the stability for a long time of a final product. That is, the increase of the volatile loss means the decrease of the amount of the ester-based composition (plasticizer) present in the specimen and the deterioration of the elongation rate.

Thus, it may be secured that the physical properties of the isophthalate-based ester plasticizer of the present invention be markedly increased when compared to those of a terephthalate-based and phthalate-based plasticizers.

Preparation Example 6, Examples, Comparative Examples and Experimental Examples

Preparation Example 6

To a four-necked, 3 liter reactor equipped with a cooler, a water stripper, a condenser, a decanter, a reflux pump, a temperature controller, a stirrer, etc., 498.4 g of purified isophthalic acid (PIA), 1,298.3 g of isononyl alcohol (CAS No. 68526-84-1 of EXXONMOBILE Co.) (molar ratio of isophthalic acid:isononyl alcohol was 1:3) and 1.54 g of tetra isopropyl titanate (TIPT) as a titanium-based catalyst were inserted, followed by slowly elevating the temperature to about 170° C. The generation of water began at about 170° C. An esterification reaction was conducted at the reaction temperature of about 220° C. under an atmospheric pressure while continuously injecting a nitrogen gas for about 4.5 hours, and the reaction was terminated when an acid value reached 0.01.

After completing the reaction, distillation-extraction under a reduced pressure was conducted for 0.5 to 4 hours to remove unreacted raw materials. The reactant was cooled, and neutralization treatment was conducted using an alkaline solution. In addition, the reactant was dehydrated to remove water. A filter medium was inserted to the dehydrated reactant, followed by stirring for a certain time and filtering to finally obtain 1,243.3 g of di-isononyl isophthalate (yield 99.0%).

Example 22

To a reactor equipped with a stirrer, a condenser and a decanter, 1,000 g of di-isononyl isophthalate (hereinafter, DINIP) prepared in Preparation Example 6 and 70 g of butanol (7 parts by weight on the basis of 100 parts by weight of DINIP) were added, and a trans-esterification reaction was conducted under a nitrogen atmosphere at the reaction temperature of 140° C. for 5 hours without a catalyst to produce an ester-based composition including 21.3 wt %, 2.3 wt % and 77.2 wt % of the compounds of the following Formula 2-3, Formula 1-1 and Formula 3-3, respectively.

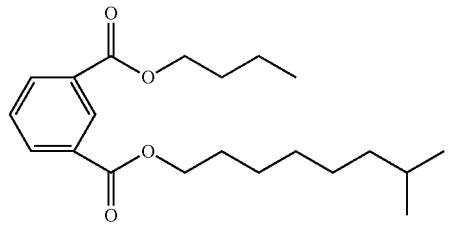
<Formula 2-3>

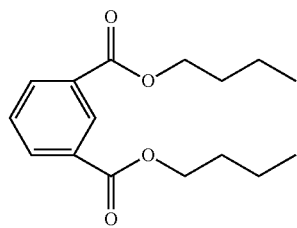
<Formula 1-1>

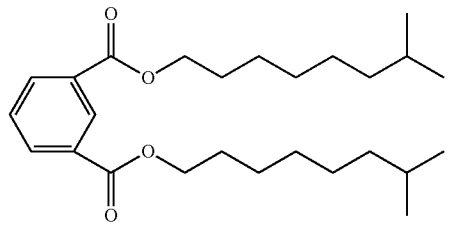
<Formula 3-3>

The above reaction products were mixed distillated to remove butanol and isononyl alcohol to finally prepare an ester-based composition.

Examples 23 to 29

Ester-based compositions having the compositions of Formula 2-3, Formula 1-1 and Formula 3-3 in the following Table 8 were obtained by conducting the same procedure described in Example 22 except for controlling the amount of butanol as described in the following Table 8.

Comparative Example 6 (Terephthalate-based)

A reaction product including 75.1 wt % of di-(isononyl) terephthalate (DINTP), 23.0 wt % of 1-butyl 4-(isononyl)

terephthalate (hereinafter, BINTP) and 1.9 wt % of dibutyl terephthalate (hereinafter, DBTP) was obtained by conducting the same procedure described in Preparation Example 3 and Example 22 using terephthalic acid instead of isophthalic acid prepared in Preparation Example 3.

Comparative Example 7 (Phthalate-based)

A reaction product including 75.9 wt % of di-(isononyl) phthalate (DNIP), 22.0 wt % of 1-butyl 4-(isononyl)phthalate (hereinafter, BINP) and 2.1 wt % of dibutyl phthalate (hereinafter, DBP) was obtained by conducting the same procedure described in Preparation Example 3 and Example 22 using phthalic acid instead of isophthalic acid prepared in Preparation Example 3.

TABLE 8

| | Butanol amount (parts by weight) | Formula 1-1 (wt %) | Formula 2-3 (wt %) | Formula 3-3 (wt %) |
|---|---|---|---|---|
| Example 22 (1P) | 7 parts by weight | Formula 1-1 (2.3) | Formula 2-3 (20.5) | Formula 3-3 (77.2) |
| Example 23 (1P) | 4 parts by weight | Formula 1-1 (0.7) | Formula 2-3 (14.9) | Formula 3-3 (84.4) |
| Example 24 (1P) | 10 parts by weight | Formula 1-1 (2.9) | Formula 2-3 (28.9) | Formula 3-3 (68.2) |
| Example 25 (1P) | 15 parts by weight | Formula 1-1 (5.0) | Formula 2-3 (35.3) | Formula 3-3 (59.7) |
| Example 26 (1P) | 20 parts by weight | Formula 1-1 (7.9) | Formula 2-3 (41.3) | Formula 3-3 (51.8) |
| Example 27 (1P) | 25 parts by weight | Formula 1-1 (10.5) | Formula 2-3 (43.8) | Formula 3-3 (45.7) |
| Example 28 (1P) | 30 parts by weight | Formula 1-1 (12.2) | Formula 2-3 (45.8) | Formula 3-3 (42.0) |
| Example 29 (1P) | 40 parts by weight | Formula 1-1 (18.0) | Formula 2-3 (49.8) | Formula 3-3 (32.2) |
| Comparative Example 6 (TP) | 7 parts by weight | (DBTP) (1.9) | (BINTP) (23.0) | (DINTP) (75.1) |
| Comparative Example 7 (P) | 7 parts by weight | (DBP) (2.1) | (BINP) (22.0) | (DINP) (75.9) |

Experimental Example 5

Measuring Amount of Ester-based Composition

In the ester-based compositions of Examples 22 to 29 of the present invention and Comparative Examples 6 to 7, the amount (wt %) of each compound was measured using a gas chromatography apparatus of Agilent Co. (Agilent 7890 GC, column: HP-5, carrier gas: helium).

In the ester-based compositions of Examples 22 to 29, ether was not detected.

Experimental Example 6

Manufacture of Specimen and Evaluation of Performance

For the ester-based composition prepared in Examples 22 to 29 and Comparative Examples 6 to 7, 55 parts by weight of a plasticizer, 2 parts by weight of a BZ stabilizer (BZ210, Songwon Industries) as an additive and 2 parts by weight of an epoxidized soybean oil (ESO, Songwon Industries) with respect to 100 parts by weight of a polyvinyl chloride resin (PVC, LS 130s) were mixed in a rotational rate of 1,300 rpm at 100° C. A process was conducted using a roll mill at 175° C. for 4 minutes and using a press at 185° C. for 3 minutes (low pressure) and for 2 minutes and 30 seconds (high pressure) to manufacture a sheet with a thickness of 2 mm.

With respect to the sheet, hardness, tensile strength, elongation rate, migration loss and sheet volatile loss were measured. The results are illustrated in Tables 9 and 10.

TABLE 9

| | Butanol amount | Hardness (Shore A) | Tensile strength (kg/cm$^2$) | Elongation rate (%) | Migration loss (%) |
|---|---|---|---|---|---|
| Example 23 | 4 parts by weight | 90.3 | 237.5 | 291.6 | 0.05 |
| Example 24 | 10 parts by weight | 88.5 | 224.6 | 303.4 | 0.06 |
| Example 25 | 15 parts by weight | 88.2 | 220.7 | 310.2 | 0.10 |
| Example 26 | 20 parts by weight | 87.6 | 216.8 | 316.5 | 0.14 |
| Example 27 | 25 parts by weight | 86.8 | 209.5 | 321.7 | 0.16 |
| Example 28 | 30 parts by weight | 85.9 | 201.3 | 330.1 | 0.17 |
| Example 29 | 40 parts by weight | 84.5 | 195.6 | 345.6 | 0.20 |

The above Table 9 shows the hardness, tensile strength, elongation rate and migration resistance of the ester-based compositions of Examples 23 to 29 according to the amount added of butanol.

As shown in the above Table 9, the hardness, tensile strength, elongation rate and migration resistance are markedly changed according to the amount added of butanol.

Particularly, the hardness, tensile strength and elongation rate are relatively improved while the migration resistance is decreased according to the decrease of the amount added of butanol.

Accordingly, the physical properties may be controlled according to use by controlling the amount of butanol, and it may be secured that the ester-based compositions may be usefully applied.

TABLE 10

| | | Example/Comparative example | | |
|---|---|---|---|---|
| | | Example 22 | Comparative Example 6 | Comparative Example 7 |
| Acid | | Isophthalic acid | Terephthalic acid | Phthalic acid |
| Reaction | | Trans-esterification | Trans-esterification | Trans-esterification |
| Physical properties | Hardness (Shore A) | 88.5 | 89.5 | 88.3 |
| | Tensile strength (kg/cm$^2$) | 225.7 | 254.6 | 220.9 |
| | Elongation rate (%) | 290.6 | 240.8 | 284.3 |
| | Migration loss (%) | 0.05 | 0.09 | 0.04 |
| | Volatile loss (%) | 1.02 | 1.45 | 1.23 |

Table 10 shows the results of the hardness, tensile strength, elongation rate and migration resistance of the sheets manufactured using the plasticizers of Example 22 and Comparative Examples 6 and 7 by changing the kinds of an acid.

As shown in the above Table 10, the elongation rate is improved, and the effects of migration resistance and volatile loss are good for the ester-based composition of the example of the present invention using an isophthalate-based ester plasticizer when compared to the ester-based compositions of Comparative Examples 6 and 7 using terephthalate-based and phthalate-based ester plasticizers.

Particularly, for the specimen using the isophthalate-based ester plasticizer of the present invention, the elongation rate, migration resistance and volatile loss are improved when compared to the phthalate-based and terephthalate-based ester plasticizer having ester groups at ortho position and para position. Thus, the processability of a resin, absorption rate with the resin, the degree of migration loss and heat stability are improved.

In addition, the volatile loss of the specimen of Example 22 of the present invention may decrease to about 20 to 45% when compared to that of Comparative Examples 6 and 7.

The increase of the volatile loss as in Comparative Examples 6 and 7 may be a fatal defect in the processability and the stability for a long time of a final product. That is, the increase of the volatile loss means the decrease of the amount of the ester-based composition (plasticizer) present in the specimen and the deterioration of the elongation rate.

Thus, it may be secured that the physical properties of the isophthalate-based ester plasticizer composition of the present invention may be markedly increased when compared to a terephthalate-based and phthalate-based plasticizers.

The invention claimed is:
1. An ester-based composition comprising compounds of the following Formula 1, Formula 2 and Formula 3:

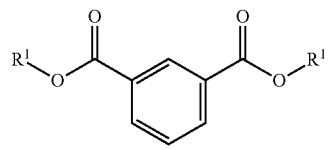

<Formula 1>

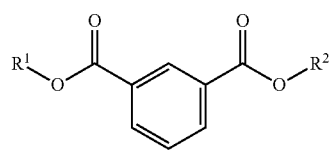

<Formula 2>

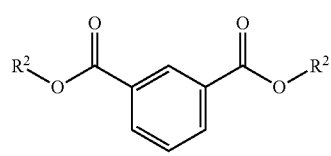

<Formula 3> wherein, in the above Formulae 1 to 3, $R^1$ and $R^2$ are independently $C_1$-$C_{20}$ alkyl, and $R^1$ and $R^2$ are not the same, and
wherein $R^1$ is non-branch type alkyl, and $R^2$ is branch-type alkyl.

2. The ester-based composition of claim 1, wherein $R^2$ comprises more carbon atoms than $R^1$.

3. The ester-based composition of claim 2, wherein $R^1$ is $C_3$-$C_{10}$ alkyl, and $R^2$ $C_6$-$C_{12}$ alkyl.

4. The ester-based composition of claim 3, wherein $R^1$ is $C_3$-$C_5$ alkyl, and $R^2$ is $C_6$-$C_{12}$ alkyl.

5. The ester-based composition of claim 4, wherein $R^2$ is selected from ethylhexyl, isononyl and propylheptyl.

6. The ester-based composition of claim 1, wherein the compounds of Formula 1, Formula 2 and Formula 3 are comprised in amounts of 0.5 to 50 wt %, 0.5 to 70 wt % and 0.5 to 85 wt % with respect to a total amount of the ester-based composition.

7. The ester-based composition of claim 6, wherein the compounds of Formula 1, Formula 2 and Formula 3 are comprised in amounts of 0.5 to 50 wt %, 10 to 50 wt % and 35 to 80 wt % with respect to a total amount of the ester-based composition.

8. The ester-based composition of claim 6, wherein a ratio of a total amount of the compounds of Formulae 1 and 3 and an amount of the compound of Formula 2 is 95:5 to 30:70 by weight.

9. The ester-based composition of claim 1, wherein the ester-based composition comprises compounds of the following Formula 1-1, Formula 2-1 and Formula 3-1:

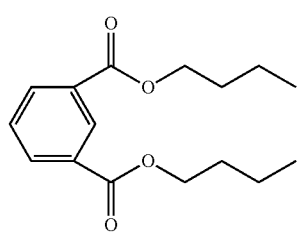

<Formula 1-1>

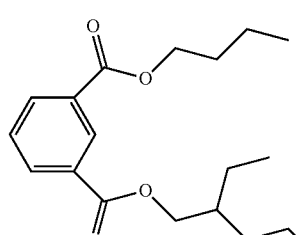

<Formula 2-1>

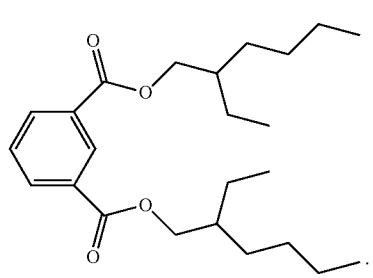

<Formula 3-1>

10. The ester-based composition of claim 1, wherein the ester-based composition comprises compounds of the following Formula 1-1, Formula 2-2 and Formula 3-2:

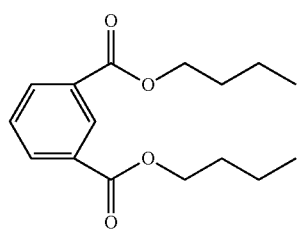

<Formula 1-1>

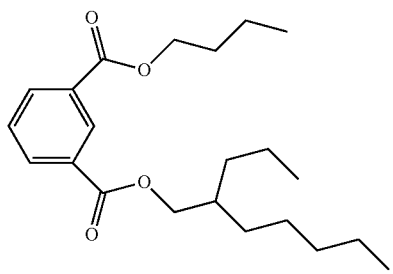
<Formula 2-2>

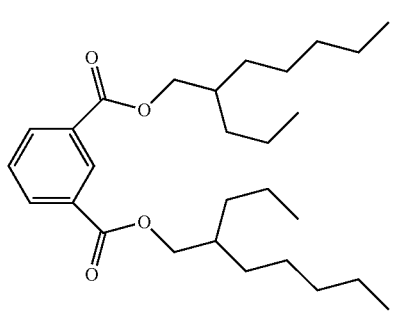
<Formula 3-2>

11. The ester-based composition of claim 1, wherein the ester-based composition comprises compounds of the following Formula 1-1, Formula 2-3 and Formula 3-3:

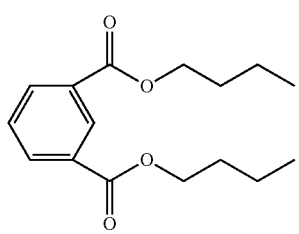
<Formula 1-1>

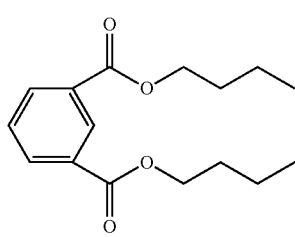
<Formula 2-3>

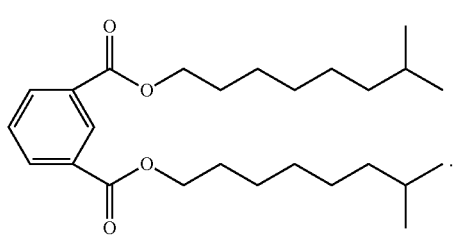
<Formula 3-3>

12. The ester-based composition of claim 1, wherein the ester-based composition comprises compounds of the following Formula 1-1, Formula 2-4 and Formula 3-4:

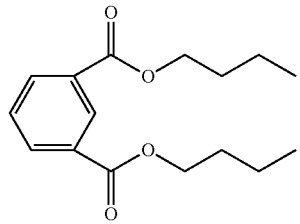
<Formula 1-1>

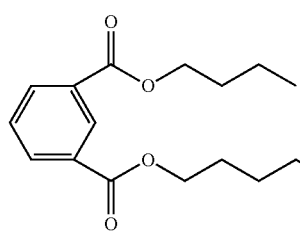
<Formula 2-4>

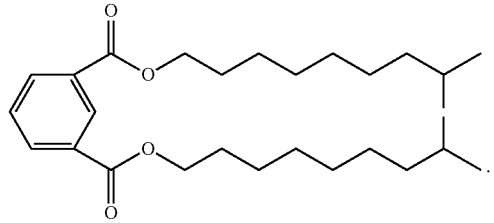
<Formula 3-4>

13. The ester-based composition of claim 1, wherein the ester-based composition is an ether-free plasticizer.

14. A method of preparing the ester-based composition of claim 1 comprising conducting a trans-esterification reaction of a compound of the following Formula 3 with a first alcohol of the following Formula 4:

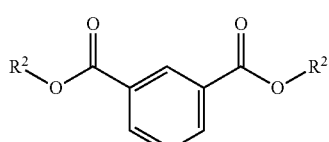
<Formula 3>

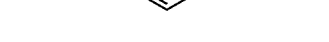
<Formula 4> in the above formulae, $R^1$ and $R^2$ are independently $C_1$-$C_{20}$ alkyl, and $R^1$ and $R^2$ are not the same, and wherein $R^1$ is non-branched type alkyl, and $R^2$ is branched-type alkyl.

15. The method of the ester-based composition of claim 14, wherein a molar ratio of the compound of the above Formula 3 and a first alcohol of the above Formula 4 is 1:0.005 to 5.

16. The method of the ester-based composition of claim 14, wherein an amount of the first alcohol of the above Formula 4 is 0.1 to 89.9 parts by weight with respect to 100 parts by weight of the compound of the above Formula 3.

17. The method of the ester-based composition of claim 14, wherein the trans-esterification reaction is a non-catalytic reaction.

18. The method of the ester-based composition of claim 14, further comprising distilling unreacted first alcohol of Formula 4 and by-products to remove after the trans-esterification reaction.

19. The method of the ester-based composition of claim 14, wherein a portion of the compound of the above Formula 3 is transformed into a compound of the following Formula 1 and a compound of the following Formula 2:

<Formula 1>

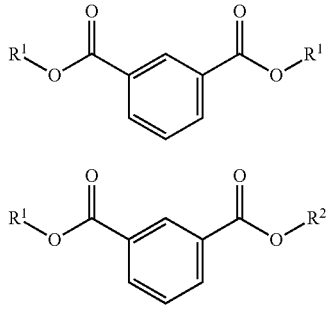

<Formula 2> in the above formulae, $R^1$ and $R^2$ are independently $C_1$-$C_{20}$ alkyl, and $R^1$ and $R^2$ are not the same.

20. The method of the ester-based composition of claim 14, wherein the compound of the above Formula 3 is obtained by an esterification reaction of a compound of the following Formula 5 and a second alcohol of the following Formula 6 in the presence of a catalyst:

<Formula 5>

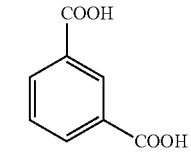

<Formula 6>

$R^2$—OH in the above formula, $R^2$ is $C_1$-$C_{20}$ alkyl.

21. The method of the ester-based composition of claim 20, wherein the compound of the above Formula 5 and the second alcohol of the above Formula 6 are used in a molar ratio of 1:1 to 7.

22. The method of the ester-based composition of claim 20, wherein the second alcohol of the above Formula 6 further comprises at least one isomer of the second alcohol.

* * * * *